United States Patent [19]

Drent

[11] Patent Number: 4,806,693

[45] Date of Patent: Feb. 21, 1989

[54] PROCESS FOR THE PREPARATION OF UNSATURATED KETONES

[75] Inventor: Eit Drent, Amsterdam, Netherlands

[73] Assignee: Shell Oil Company, Houston, Tex.

[21] Appl. No.: 104,147

[22] Filed: Oct. 5, 1987

Related U.S. Application Data

[62] Division of Ser. No. 899,182, Aug. 22, 1986, Pat. No. 4,727,195.

[30] Foreign Application Priority Data

Sep. 27, 1985 [GB] United Kingdom ............... 8523858

[51] Int. Cl.$^4$ .............................................. C07C 49/21
[52] U.S. Cl. ................................................. 568/417
[58] Field of Search ........................................ 568/417

[56] References Cited

U.S. PATENT DOCUMENTS

| | | | |
|---|---|---|---|
| 2,562,393 | 7/1951 | Reppe et al. | 260/533 |
| 3,020,314 | 2/1962 | Alderson | 260/597 |
| 3,059,031 | 10/1962 | Alderson | 260/597 |
| 3,494,959 | 2/1970 | Schleppnik et al. | 568/417 |
| 3,513,202 | 5/1970 | Chretien et al. | 260/593 |
| 3,676,499 | 7/1972 | Redel et al. | 568/417 |
| 3,876,672 | 4/1975 | Mrowca | 260/410.9 R |

FOREIGN PATENT DOCUMENTS 1056083  1/1967  United Kingdom ............... 568/417

OTHER PUBLICATIONS

Vartanyan et al., Chem. Abst., vol. 60, #11969g (1964).
Tishchenko et al., Chem. Abst., vol. 65, #8196a (1966).
Tokmuryin et al., Chem. Abst., vol. 105, #152935h (1986).
Vartanyan et al., Chem. Abst., vol. 66, #10634p (1967).
Malacria et al., Tetrahedron 33 (1977) 2813–2817.
Shulyakovskii et al., Chem. Abst., vol. 96, 103595j (1982).
Liner et al., Chem. Abst., vol. 98, #178491X (1983).
Moiseev et al., Chem. Abst., vol. 98, #114390f (1983).

*Primary Examiner*—James H. Reamer

[57] ABSTRACT

A process for preparing compounds of the general formula

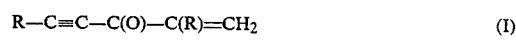

R represents an H atom or an optionally substituted hydrocarbyl group, by reacting a compound R—C≡CH with CO in the presence of a Pd(II) compound, an organic phosphine and a protonic acid having a $pK_a$ below 3.0.

Compounds of formula I in which R represents an optionally substituted hydrocarbyl group are novel.

1 Claim, No Drawings

PROCESS FOR THE PREPARATION OF UNSATURATED KETONES

This is a division of application Ser. No. 899,182, filed Aug. 22, 1986 now U.S. Pat. No. 4,727,195.

FIELD OF THE INVENTION

The invention relates to a process for the preparation of acetylenically and ethylenically unsaturated ketones. The invention also relates to unsaturated ketones.

BACKGROUND OF THE INVENTION

Acetylenically and ethylenically unsaturated ketones may be used as a starting material for the preparation of jasmone-type compounds and of polymers. The synthesis of one of such ketones, 1-pentene-3-one-4-yne, is described in Tetrahedron 33 (1977) 2813-2817, but this synthesis is very complicated. It has now been found that such ketones can be prepared with high selectivity and in an acceptable yield using relatively simple starting compounds.

SUMMARY OF THE INVENTION

The invention relates to a process for the preparation of acetylenically and ethylenically unsaturated ketones of the general formula I:

$$R-C\equiv C-\underset{\underset{R}{|}}{\underset{\|}{C}}-C=CH_2 \qquad (I)$$
$$\phantom{R-C\equiv C-}O$$

in which R represents a hydrogen atom or an optionally substituted hydrocarbyl group, which process comprises reacting an acetylenically unsaturated compound of the general formula II:

$$R-C\equiv CH \qquad (II)$$

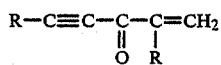

in which R has the same meaning as in the general formula I with carbon monoxide in the presence of a catalytic system formed by combining:
(a) a compound of divalent palladium,
(b) an organic phosphine, and
(c) a protonic acid having a $pK_a$ below 3.0 (measured at 18° C. in aqueous solution), with the exception of carboxylic acids.

DESCRIPTION OF THE PREFERRED EMBODIMENTS

The two optionally substituted hydrocarbyl groups represented by R in the general formula I are the same, preferably optionally substituted alkyl groups, and more preferably alkyl groups having in the range of from 1 to 10 carbon atoms. Very good results have been obtained using propyne as the compound of the general formula II, R representing a methyl group. Any substituent on the hydrocarbyl group represented by R must be inert in the process according to the invention. Examples of such substituents are cyano, ester, alkoxy and aryl groups and halogen atoms, in particular, fluorine atoms. Other examples of hydrocarbyl groups are aryl, alkyl-substituted aryl groups and aryl-substituted alkyl groups. Examples of other very suitable compounds of the general formula II are ethyne, 1-butyne, 1-pentyne, 1-hexyne, 1-heptyne, 1-octyne, 1-nonyne, 1-decyne, benzylethyne and cyclohexylethyne.

Both homogeneous and heterogeneous palladium catalysts may be used in the process according to the invention. Homogeneous catalysts are preferred. Suitable homogeneous catalysts are the salts of palladium with, for example, nitric acid, sulfuric acid or, particularly, alkanoic acids; among the alkanoic acids those having not more than 12 carbon atoms per molecule are preferred. Very good results have been obtained with palladium acetate. Moreover, palladium complexes may be used, for example palladium acetylacetonate, tetrakistriphenylphosphinepalladium, bis-tri-o-tolylphosphinepalladium acetate or bistriphenylphosphinepalladium sulfate. Palladium bonded to an ion exchanger, for instance an ion exchanger comprising sulfonic acid groups, is an example of a suitable heterogeneous catalyst.

Suitable organic phosphines which may be used in the process according to the invention include those of the general formula III:

$$R^1-\underset{\underset{R^2}{|}}{P}-R^3 \qquad (III)$$

in which $R^1$ represents an optionally substituted aryl group and $R^2$ and $R^3$ each an optionally substituted alkyl, optionally substituted cycloalkyl or optionally substituted aryl group, or $R^2$ and $R^3$ together represent an optionally substituted alkylene or phosphacycloalkylene group. Preferably the alkyl group has up to 20 carbon atoms, the cycloalkyl group up to 5 to 7 carbon atoms in the ring and the aryl group up to 18 carbon atoms in the ring. The aryl group may be an anthryl, naphthyl or, preferably a phenyl group. Phosphines of the general formula I, in which $R^1$ and $R^2$ each represent an optionally substituted phenyl group are a preferred group of phosphines. The phosphines of this group in which $R^3$ also represents an optionally substituted phenyl group are particularly preferred. Very good results have been obtained with triphenylphosphine.

Examples of non-carboxylic acids having a pKa below 3.0 are orthophosphoric acid, pyrophosphoric acid, arsenic acid and benzenephosphonic acid, with benzenephosphonic acid being preferred.

The quantity of the compound of divalent palladium to be used in the process according to the invention is not critical and may vary within wide limits. Preference is given to the use of quantities in the range between $10^{-5}$ and $10^{-1}$ gram atom palladium per mol of compound of the general formula II.

The molar ratio of organic phosphine to palladium is not critical and may vary within wide limits. If less than 5 mol of the organic phosphine are used per gram atom of palladium, selectivity to compounds of the general formula I is still very high, but the reaction rate is moderate. Very high selectivities and very high reaction rates are obtained when more than 5 mol and in particular more than 20 mol of the organic phosphine are used per gram atom of palladium. In general, more than 500 mol of the organic phosphine per gram atom of palladium need not be used.

The number of equivalents of the organic phosphine which is used per equivalent of protonic acid having a $pK_a$ below 3.0 (with the exception of carboxylic acids) is not critical and may vary within wide limits. This number is suitably in the range of from 0.5 to 50.

The process according to the present invention is suitably carried out in the presence of a solvent for the compounds of the general formula I. A suitable solvent may, for example, be selected from aromatic hydrocarbons, for example benzene, toluene, ethylbenzene and the three xylenes; ketones, for example acetone or methyl isobutyl ketone; sulfoxides, for example dimethyl sulfoxide and diethyl sulfoxide; sulfones, for example diisopropyl sulfone and tetrahydrothiophene 1,1-dioxide (also referred to as "sulfolane") and ethers, for example anisole, 2,5,8-trioxanonane (also referred to as "diglyme", diphenyl ether and diisopropyl ether.

The process according to the invention permits the use of very mild reaction conditions. Temperatures in the range of from 50° C. to 200° C., especially 100° C. to 150° C., are generally suitable. The pressure may vary over a wide range. Generally, a pressure in the range of from 1 to 100 bar is suitable, with pressures of from 5 to 50 bar being preferred. Pressures higher than 100 bar may be used, but are usually economically unattractive.

The molar ratio of compound of the general formula II to carbon monoxide is not critical and may vary between wide limits. Generally, the ratio is in the range of from 0.05 to 1.

Compounds of the general formula:

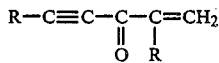

in which R represents an optionally substituted hydrocarbyl group are novel. Examples of such optionally substituted hydrocarbyl groups are optionally substituted alkyl groups, for instance those having in the range of from 1 to 10 carbon atoms. 2-Methyl-1-hexene-3-one-4-yne is an example of such a compound.

The invention is further described by means of the following examples which are intended for illustration and are not to be construed as limiting the invention. The selectivity to a certain compound, expressed in a percentage, is defined as 100 a/b, in which "a" is the amount of acetylenically unsaturated compound of the general formula II that has been converted into that certain compound and "b" is the total amount of that acetylenically unsaturated compound that has been converted.

EXAMPLE 1

A 250 ml magnetically stirred Hastelloy C autoclave ("Hastelloy" is a trade name) was charged with toluene (50 ml), acetone (20 ml), methacrylic acid ($pK_a>4.0$, 1 ml), palladium acetate (0.2 mmol), triphenylphosphine (10 mmol) and benzenephosphonic acid ($C_6H_5H_2PO_3$, $pK_a=1.8$, 10 mmol), 0.001 gram atom Pd per mol of propyne being used. The autoclave was flushed with carbon monoxide, filled with propyne and carbon monoxide until partial pressures of 2 bar and 20 bar, respectively, were reached and heated to a temperature of 115° C.

After a reaction time of 2.5 h at 115° C., the contents of the autoclave were analyzed by means of gas-liquid chromatography. The conversion of propyne was 60% with a selectivity to 2-methyl-1-hexene-3-one-4-yne of 78%. The mass spectrum of the latter compound was obtained by electron impact ionization using 70 electron volt electrons with the emission current at point 30 milliampere and keeping the source temperature at 200° C. The used GC/MS combination, a Finnigan 4000 was scanning a mass range of 20–650 daltons at a rate of one second a scan. The mass spectrum was normalized with the largest peak above M/E 35 set to 100° C. The eight largest peaks were used, thereby ignoring background peaks at M/E 28, 32, 40 and 44, due to residual air in the instrument. The mass spectrum of 2-methyl-1-hexene-3-one-4-yne consists of the following points:

| M/E | % Intensity | M/E | % Intensity |
|-----|-------------|-----|-------------|
| 67  | 100         | 80  | 17          |
| 108 | 70          | 77  | "           |
| 39  | 50          | 38  | "           |
| 79  | 18          | 41  | "           |

EXAMPLE 2

The procedure described in Example 1 was repeated with the difference that 0.5 ml of methacrylic acid instead of 1 ml and 12.5 mmol of benzenephosphonic acid instead of 10 mmol were used. After a reaction time of 5 h at 115° C. the conversion of propyne was 80% with a selectivity to 2-methyl-1-hexene-3-one-4-yne of 75%.

EXAMPLE 3

The procedure described in Example 1 was repeated with the difference that methacrylic acid and benzenephosphonic acid were not present and that orthophosphoric acid (10 mmol, $pK_a=2.2$) was used. After a reaction time of 5 h at 115° C. the conversion of propyne was 30% with a selectivity to 2-methyl-1-hexene-3-one-4-yne of 85%.

COMPARATIVE EXPERIMENT A

The procedure described in Example 1 was repeated with the difference that benzenephosphonic acid was not present. After a time of 5 h at 115° C. the conversion of propyne was less than 5%.

EXAMPLE 4

The procedure described in Example 1 was repeated with the difference that benzenephosphonic acid (10 mmol) was replaced with p-toluenesulfonic acid (10 mmol). After a reaction time of 5 h at 115° C. the conversion of propyne was 30% with a selectivity to 2-methyl-1-hexene-3-one-4-yne of 55%.

I claim:
1. 2-Methyl-1-hexene-3-one-4-yne.

* * * * *